US007609802B2

(12) United States Patent
Langan et al.

(10) Patent No.: US 7,609,802 B2
(45) Date of Patent: Oct. 27, 2009

(54) METHOD AND SYSTEM FOR RECONSTRUCTING IMAGE VOLUMES FROM HELICAL SCAN ACQUISITIONS

(75) Inventors: David Allen Langan, Clifton Park, NY (US); Peter Michael Edic, Albany, NY (US); Xiaoye Wu, Rexford, NY (US); Jed Douglas Pack, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 251 days.

(21) Appl. No.: 11/740,002

(22) Filed: Apr. 25, 2007

(65) Prior Publication Data

US 2008/0267476 A1 Oct. 30, 2008

(51) Int. Cl.
*A61B 6/00* (2006.01)

(52) U.S. Cl. .......... 378/4; 378/15

(58) Field of Classification Search .......... 378/4, 378/15

See application file for complete search history.

(56) References Cited

U.S. PATENT DOCUMENTS 6,256,366 B1 7/2001 Lai
6,285,733 B1 * 9/2001 Proksa et al. .......... 378/15
6,415,012 B1 * 7/2002 Taguchi et al. .......... 378/15
6,418,184 B1 * 7/2002 Wang et al. .......... 378/15

OTHER PUBLICATIONS

Turbell et al., Helical Cone-Beam Tomography, Image Processing Laboratory, Department of Electrical Engineering, Linkoping University, 2000, pp. 91-100.*

Tang et al., A three-dimensional-weighted cone beam filtered backprojection (CB-FBP) algorithm for image reconstruction in volumetric CT—helical scanning, Physics in Medicine and Biology, 51, 2006, pp. 855-874.*

* cited by examiner

*Primary Examiner*—Edward J Glick
*Assistant Examiner*—Alexander H Taningco
(74) *Attorney, Agent, or Firm*—Joseph J. Christian

(57) ABSTRACT

A method, computed tomography (CT) system and computer-readable medium for reconstructing an image volume of an object scanned in helical mode. An embodiment of the method includes determining discrete focal lengths within an imaging plane of the reconstructed field of view comprising the image volume; generating a circular scan sinogram(s) for the discrete focal lengths by interpolating the helical views; selecting within a backprojection operation a circular scan sonogram(s), for one or more image points within the imaging plane, over one or more circular views. The method then includes using the selected circular scan sinogram(s), in the backprojection of the image points point(s) over the circular views view(s) and performing a backprojection for all the image points over all the circular views to generate a reconstructed image of the object.

23 Claims, 7 Drawing Sheets

Obtain helical views corresponding to image volume — 72

Define discretized focal lengths within field of view comprising image volume — 74

Generate circular scan sinograms for discretized focal lengths — 76

Select circular scan sinogram based on discretized focal lengths, wherein the selection is performed within a backprojection operation for one or more image points over one or more of the circular views — 78

Use selected circular scan sinogram in the backprojection of one or more of the image points over one or more of the circular views — 80

Perform backprojection for the one or more image points, over the one or more circular views to generate a reconstructed image of the object — 82

METHOD AND SYSTEM FOR RECONSTRUCTING IMAGE VOLUMES FROM HELICAL SCAN ACQUISITIONS

BACKGROUND

The invention relates generally to the field of image reconstruction in computed tomography (CT) imaging systems and more particularly to a method and system for reconstructing image volumes from helical scan acquisitions.

CT systems operate by projecting fan-shaped or cone-shaped X-ray beams through an object. The X-ray beams are generated by an X-ray source, and are generally collimated prior to passing through the object being scanned. The attenuated beams are then detected by a detector. The detector produces a signal based on the intensity of the attenuated X-ray beams, and the signals are processed to produce projection data. CT systems acquire data continuously, at discrete image view frames corresponding to specific angular positions, as the source and detector rotate about the object being scanned.

In helical cone-beam CT systems, the X-ray source and the detectors are mounted on a rotating gantry while the object is moved axially at a uniform rate. In helical modes of operation, the X-ray source and detector describe a helical trajectory relative to the object; the detector measures the transmitted radiation on a part of a cone of rays emanating from the X-ray source. The resulting data set contains a large quantity of data points indicative of the intensity of radiation received by the detector elements at each of the angular positions. Helical cone-beam CT systems have faster scan times and have the potential to cover large objects, with just a few gantry rotations, depending on the axial coverage of the detectors.

A number of exact reconstruction algorithms have been developed for the reconstruction of cone-beam projection data acquired in a helical mode. Cone-beam reconstruction algorithms are known to be mathematically exact in the absence of noise and discretization (sampling) effects, and generally produce images of high quality when used on real data. However, in some applications (such as industrial CT inspections), requiring high-throughput imaging to be performed on large objects, cone-beam reconstruction of projection data is expensive in terms of computation, data access and latency requirements.

To reduce the complexity associated with cone-beam reconstruction, image reconstruction techniques based on helical interpolation and two-dimensional (2D) Filtered Back Projection (FBP) reconstruction may be used, to interpolate one or more helical views to approximate a corresponding axial or circular view. As is known to those skilled in the art, circular or axial scan approximations of helical views retain good image quality at the center of the reconstructed image volume, typically referred to as the "iso-center". However, as the distance of the image pixel from the "iso-center" increases, the image quality decreases and circular or axial scan approximations tend to become de-focused, thereby introducing image artifacts. Therefore, image reconstruction techniques based on helical interpolation and two-dimensional (2D) FBP reconstruction, when used in a manner as described above, may introduce image artifacts, particularly, in systems with topologies requiring a large field of view and large detector extent or axial coverage.

It would be desirable to develop a computationally efficient technique based on helical interpolation and two-dimensional (2D) FBP reconstruction algorithms, for the reconstruction of large image volumes in high-throughput applications. In addition, it would be desirable to develop a computationally efficient technique for the reconstruction of large image volumes acquired from helical scan acquisitions, with reduced image artifacts and optimized image quality throughout the field of view.

BRIEF DESCRIPTION

In one embodiment, a method and computer-readable medium for reconstructing an image volume of an object scanned in helical mode is provided. The method and computer-readable medium include obtaining one or more helical views corresponding to an image volume of an object and determining a plurality of discrete focal lengths within an imaging plane of a reconstructed field of view comprising the image volume. The method then comprises generating a plurality of circular or axial scan sinograms for the plurality of discrete focal lengths. The plurality of circular scan sinograms are generated by interpolating the helical views. The method then comprises selecting one or more circular scan sinograms from the plurality of circular scan sinograms, based on the focal lengths, wherein the selection is performed within a backprojection operation, for one or more image points, over one or more circular views. The method further comprises using one or more of the selected circular scan sinograms, in the backprojection of one or more of the image points over one or more of the circular views. The method finally comprises performing a backprojection for all the image points, over all the circular views to generate a reconstructed image of the object.

In another embodiment, a computed tomography (CT) system for reconstructing an image volume of an object scanned in helical mode is provided. The system includes an X-ray source configured to project a plurality of X-ray beams though the object from a plurality of projection angles and a detector configured to produce a plurality of electrical signals corresponding to the intensity of the X-ray beams. The system also includes a processor configured to process the electrical signals to generate one or more helical views corresponding to the imaged object. The processor is further configured to determine a plurality of discrete focal lengths within an imaging plane of a reconstructed field of view comprising the image volume and generate a plurality of circular or axial scan sinograms for the plurality of discrete focal lengths. The plurality of circular scan sinograms are generated by interpolating the helical views. The processor is then configured to select one or more circular scan sinograms from the plurality of circular scan sinograms based on the focal lengths, wherein the selection is performed within a backprojection operation, for one or more image points, over one or more circular or axial views. The processor is further configured to use one or more of the selected circular scan sinograms in the backprojection of one or more of the image points over one or more of the circular views. The processor is then configured to perform a backprojection for all the image points over all the circular views to generate a reconstructed image of the object.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
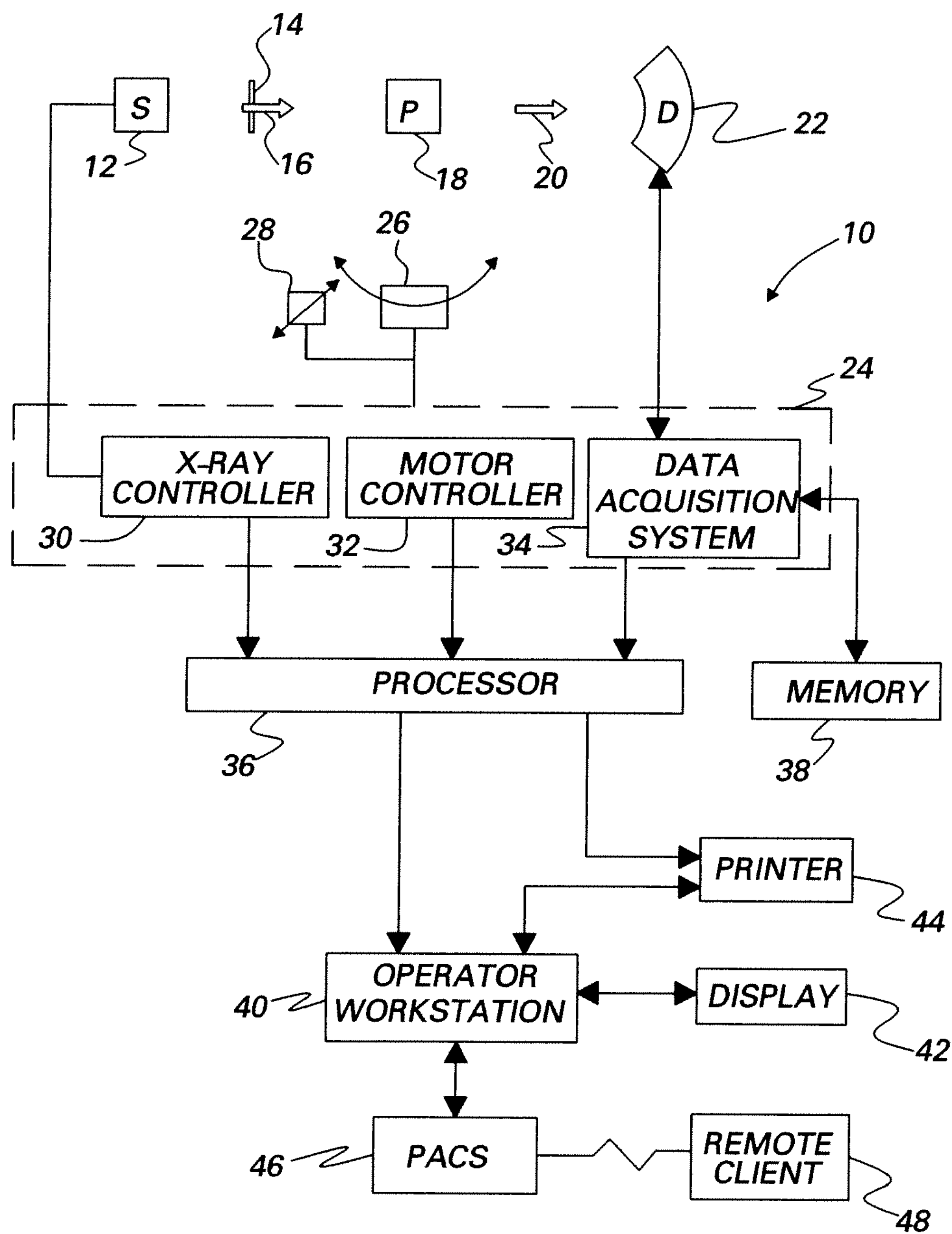
FIG. 1 is a diagrammatical view of an imaging system in the form of a CT imaging system.

FIG. 1 illustrates diagrammatically an imaging system 10 for acquiring and processing image data. System 10 is a computed tomography (CT) system designed to acquire projection data and reconstruct an image of an object 18 from cone-beam projection data taken on a helical scanning trajectory. Imaging system 10 includes a source of X-ray radiation 12 positioned adjacent to a collimator 14. In this exemplary embodiment, the source of X-ray radiation 12 is typically an X-ray tube. Collimator 14 permits a stream of radiation 16 to pass into a region in which an object 18 is positioned. A portion of the radiation 20 passes through or around the object 18 and impacts a detector array, represented generally at reference numeral 22. Detector elements of the array produce electrical signals that represent the intensity of the incident X-ray beam. These signals are acquired and processed to reconstruct an image of the features within the object 18. While the imaging system 10 is described as including an X-ray source 12 and a detector 22, it will be appreciated by those skilled in the art, that the system 10 may include multiple X-ray sources 12 and multiple detectors 22.

Source 12 is controlled by a system controller 24, which furnishes both power, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

System controller 24 is coupled to a linear positioning subsystem 28 and rotational subsystem 26. The rotational subsystem 26 enables the X-ray source 12, collimator 14 and the detector 22 to be rotated one or multiple turns around the object 18. It should be noted that the rotational subsystem 26 may include a gantry. Thus, the system controller 24 may be utilized to operate the gantry. The linear positioning subsystem 28 enables the object 18, or more specifically a table or conveyor belt, to be displaced linearly. Thus, the table may be linearly moved within the gantry to generate images of particular areas of the object 18. Additionally, as will be appreciated by those skilled in the art, the X-ray source 12 may be controlled by an X-ray controller 30 disposed within the system controller 24. Particularly, the X-ray controller 30 is configured to provide power and timing signals to the X-ray source 12. A motor controller 32 may be utilized to control the movement of the rotational subsystem 26 and the linear positioning subsystem 28.

Further, the system controller 24 is also illustrated as comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor 36. The processor 36 is typically coupled to the system controller 24. As will be described in greater detail below, the processor 36 is further configured to determine a plurality of discrete focal lengths and generate a plurality of circular or axial scan sinograms for the focus lengths. The processor 36 is further configured to select one or more circular scan sinograms, from the plurality of circular scan sinograms based on the plurality of discrete focal lengths, wherein the selection is performed within a backprojection operation, for one or more image points, over one or more circular views. The processor is further configured to use one or more of the selected circular scan sinograms in the backprojection of one or more of the image points over one or more of the circular views and perform a backprojection for all the image points over all the circular views to generate a reconstructed image of the object.

Referring to FIG. 1 again, the data collected by the data acquisition system 34 may be transmitted to the processor 36 and moreover, to a memory 38. It should be understood that any type of memory to store a large amount of data might be utilized by such an exemplary system 10. Moreover, the memory 38 may be located at this acquisition system or may include remote components for storing data, processing parameters, and routines described below. Also the processor 36 is configured to receive commands and scanning parameters from an operator via an operator workstation 40 typically equipped with a keyboard and other input devices (not shown in FIG. 1). An operator may control the system 10 via the input devices. Thus, the operator may observe the reconstructed image and other data relevant to the system from processor 36, initiate imaging, and so forth.

A display 42 coupled to the operator workstation 40 may be utilized to observe the reconstructed image and to control imaging. Additionally, the scanned image may also be printed by a printer 44 which may be coupled to the operator workstation 40. The display 42 and printer 44 may also be connected to the processor 36, either directly or via the operator workstation 40. Further, the operator workstation 40 may also be coupled to a picture archiving and communications system (PACS) 46. It should be noted that PACS 46 might be coupled to a remote client 48, radiology department information system (RIS), hospital information system (HIS) or to an internal or external network, so that others at different locations may gain access to the image and to the image data.

It further should be noted that the processor 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
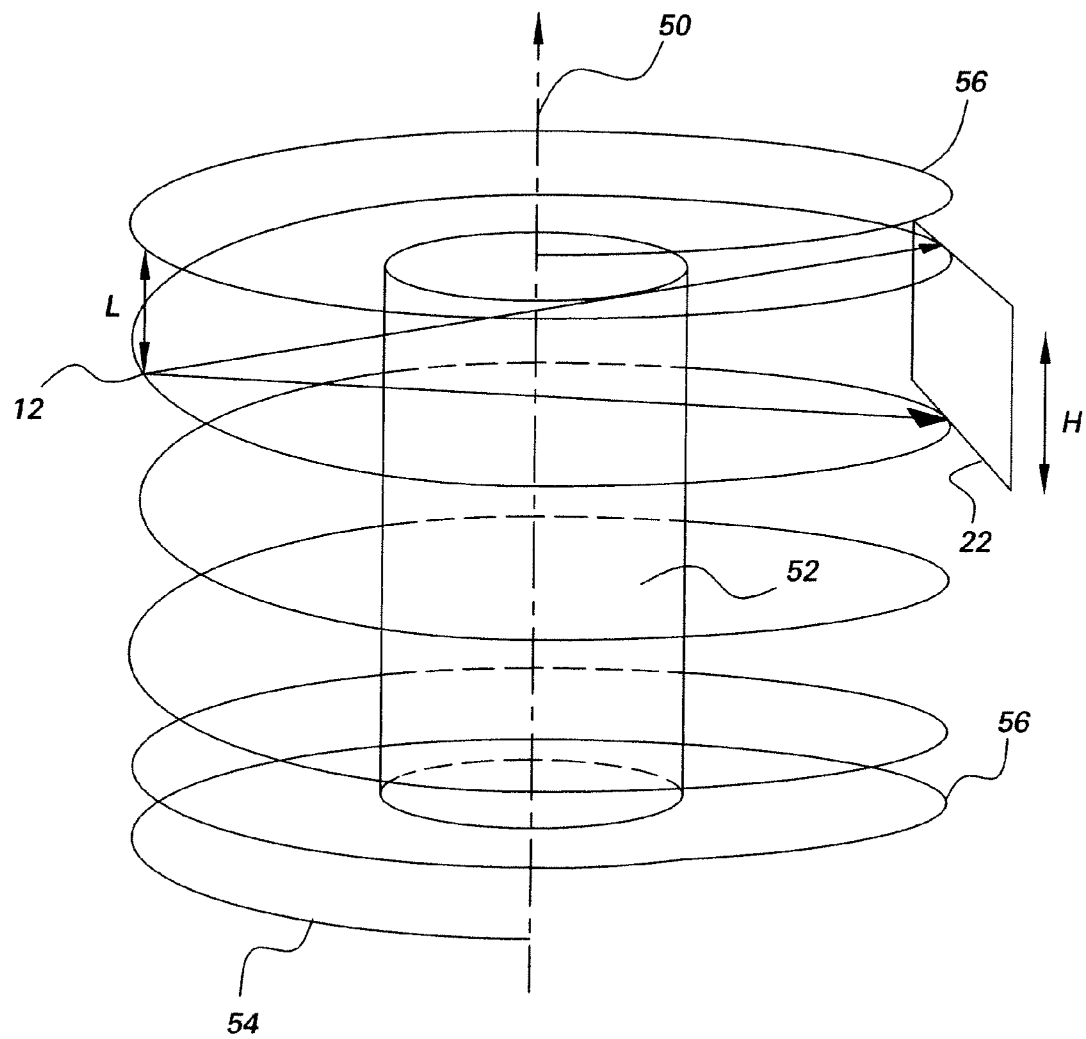
FIG. 2 is an illustration of a typical CT scanner configuration employing helical cone-beam geometry using the CT system of FIG. 1.

FIG. 2 is an illustration of a typical data acquisition configuration employing a helical cone-beam geometry using the CT system of FIG. 1. As shown in FIG. 2, a field of view 52 such as a cylinder is radially centered on an axis of rotation 50, and encloses an object to be imaged (not shown in Fig) or a subsection of an object that extends the size of the field of view 52. The X-ray energy source 12 and the detector 22 cooperate along a helical scanning trajectory 54 of the source 12 to provide cone-beam projection data. The helical scanning trajectory 54 further defines a plurality of turns or revolutions 56 about the axis of rotation 50. Typically, these turns are mutually spaced and surround the field of view 52 such that each plane passing through the field of view 52 intersects the helical scanning trajectory 54 in at least one point. For scanning the object at a plurality of angular positions, the source 12 moves relative to the object and the field of view 52 along the helical scanning trajectory 54, while the detector 22 remains fixed with respect to the source. As a result of the relative movement of the cone-beam source 12 along the helical scanning trajectory 54, the detector 22 acquires corresponding sets of cone-beam projection data to reconstruct the image of the object. As mentioned above, each set of cone-beam projection data is representative of X-ray attenuation caused by the object at different source positions. Although discussed in terms of the X-ray source 12 and detector 22 tracing a helical trajectory 54 relative to the field of view 50, the object within field of view 50 may also be translated while the X-ray source 12 and detector 22 rotate within a single axial imaging plane.

Figure 3:
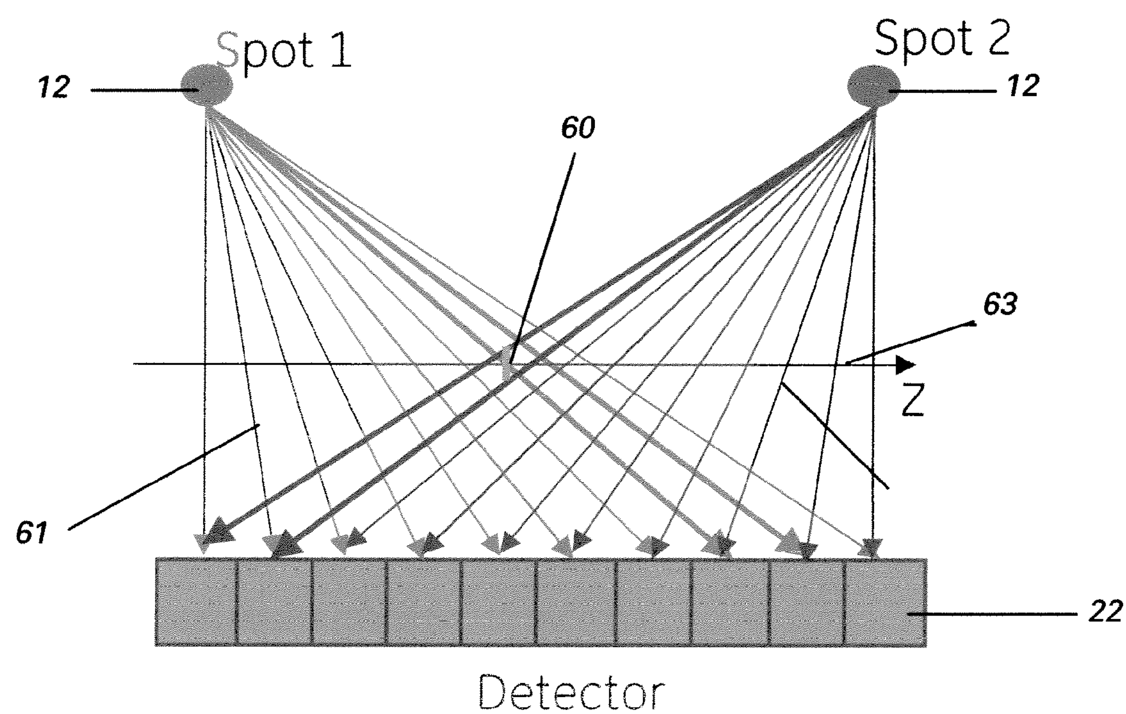
FIG. 3 is an exemplary illustration of the geometry of a plurality of rays incident on a detector from a helical scan.
Figure 4:
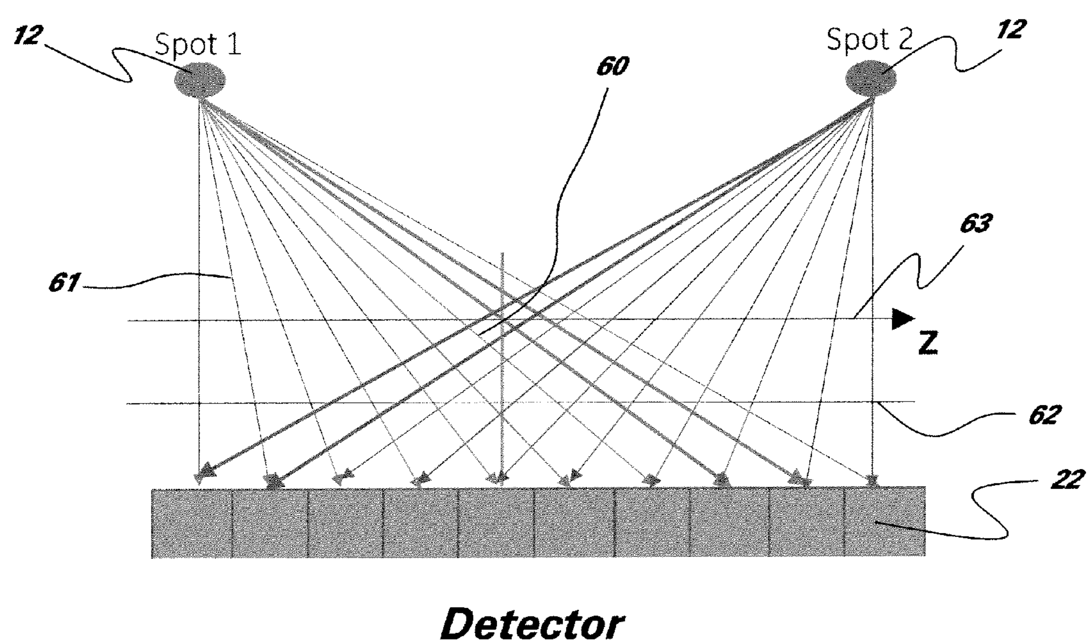
FIG. 4 is a geometric illustration of the focus limitation resulting from a helical scan to a circular or axial scan approximation.

FIG. 3 is an exemplary illustration of the geometry of a plurality of rays from a helical scan. FIG. 4 is a geometric illustration of the focus limitation resulting from a helical scan to a circular scan approximation. As shown in FIGS. 3 and 4, the X-ray source 12 projects a plurality of X-ray beams 61, at different angular positions and the detector 22 obtains a set of projection views for the imaged object (not shown in FIGS. 3 and 4) at different angular orientations of the X-ray source 12. The detector 22 may provide projection data for generating a plurality of images representative of a desired reconstructed image volume corresponding to the object. Each image of the plurality of images may correspond to a separate slice of the image volume. Referring to FIGS. 3 and 4, a z-axis 63 intersects the scanning plane at the iso-center 60, for a plurality of rays that lie in a scanning plane perpendicular to the z-axis 63. As is known to those skilled in the art, the image quality for an image slice is typically greatest at the iso-center. In the computation of a circular scan approximation, a focal length, typically the iso-center is specified in the interpolation of helical rays. Iso-center is the only point whose focal length remains constant over the helical scan. The interpolation may be performed with respect to a specific point on the z-axis, the focal point, 63. The z-axis runs parallel to the detector 22, and intersects the iso-center. In computing circular or axial scan approximations for each view angle, the rays are interpolated to represent the focal point on the plane of intersection 60. As will be appreciated by those skilled in the art, the focal point moves with table motion. Accordingly, an image slice generated from a circular scan sinogram has good image quality at the iso-center 60. The image quality of an image slice, constructed from a circular scan approximation focused at the iso-center 60, decreases for image points away from iso-center. A focal length 62 is distinct from the iso-center 60, as shown in FIG. 4. Specifically, and as may be observed in FIG. 4, if a circular scan approximation is computed for the iso-center 60, the interpolation of helical rays for the focal length 63 is clearly different from that of focal length 62.

Figure 5:
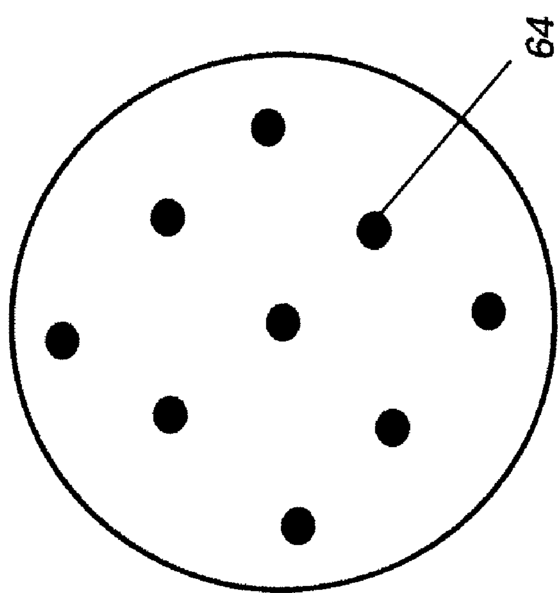
FIG. 5 is an illustration of a set of sample image points defined in a field of view within an image volume in accordance with an embodiment of the invention.

FIG. 5 is an illustration of a set of sample image points defined in a field of view within an image volume in accordance with an embodiment of the invention. As used herein, an "image point" represents a pixel to be reconstructed in the image volume. In one embodiment, a plurality of discrete focal lengths are determined. The discrete focal lengths represent a plurality of distances of the image point from the detector 22 over a rotation of the X-ray source 12 and the detector 22 about the image volume. In particular, for an image point not located at the iso-center, the distance of the image point to the detector varies over the rotation of the gantry. The image point located at the iso-center is at a constant distance to the detector over the entire rotation by definition. Consequently, an image reconstructed from an iso-center focused circular scan approximation will have greatest image quality at the iso-center. As the distance of an image point from the iso-center becomes greater, the quality of the reconstructed image point decreases.

Figure 6:
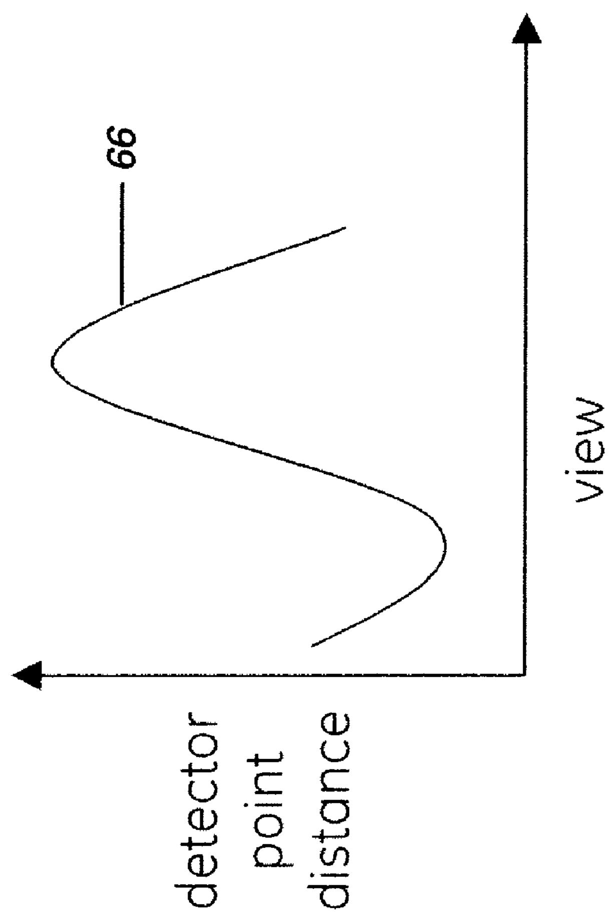
FIG. 6 is an illustration of a sinusoidal trajectory of the distance to a detector followed by a non iso-center image point, over a single rotation of the X-ray source and the detector about the image volume in accordance with an embodiment of the invention.

FIG. 6 is an illustration of a sinusoidal trajectory of the distance to a detector followed by a non iso-center image point over a single rotation of the X-ray source and the detector about the image volume, in accordance with one embodiment of the invention. In one embodiment, the plurality of discrete focal lengths are located at a plurality of focal depths along a trajectory followed by the image point over the rotation of the X-ray source and the detector about the image volume. In a particular embodiment, and as may be observed in FIG. 6, the trajectory followed by the image point is represented by a sinusoidal variation 66 of the focal lengths for the image point from the detector, over the rotation of the X-ray source and the detector about the image volume.

Figure 7:
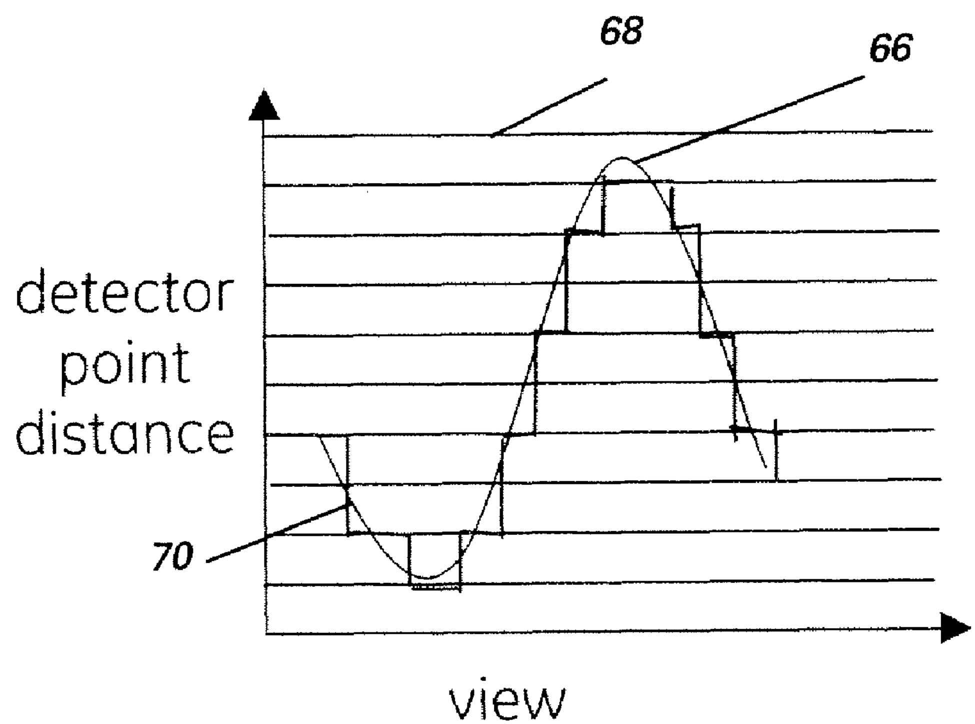
FIG. 7 is a graphical representation illustrating the mapping of a plurality of discrete focal lengths onto a trajectory followed by an image point, in accordance with an embodiment of the invention.

FIG. 7 is a graphical illustration of the mapping of a plurality of discrete focal lengths onto a trajectory followed by an image point. Circular or axial scan sinograms are computed for each focal length, in accordance with an embodiment of the invention. Referring to FIG. 7, reference numeral 68 represents circular scan sinograms generated for a constant focal length or constant distance from the detector. Reference numeral 70 represents the mapping of the image point trajectory 66 onto the discrete set of circular scan sinograms generated for candidate focal lengths.

In one embodiment, the circular scan sinograms are generated by interpolating the data collected between consecutive helical views from the X-ray source 12, using one or more helical interpolation techniques known in the art. The selection of the helical views may be made based upon the view angle position of the X-ray source and the z-axis position at which the helical views intersect the scanning plane. The interpolation is focused upon the scanning plane, which is typically selected to be iso-center since only the iso-center distance to the detector is constant over an entire acquisition rotation. As will be appreciated by those skilled in the art, when a standard two-dimensional (2D) reconstruction technique such as, for example, a 2D Filtered Back Projection (FBP) reconstruction is performed on interpolated helical scan data, the reconstructed image slice retains good image quality only in the central region. However, the image quality gets progressively unsatisfactory for regions away from the center of the image slice. This is due to the fact that an image slice reconstructed with FBP, is based on a set of interpolated projections sharing a common scanning plane extending perpendicular to the z-axis, and focused on a single focal depth, commonly the iso-center.

In accordance with one embodiment of the invention, a set of discrete focal lengths is specified over the field of view. For each focal length, a circular scan, or axial scan sinogram approximation is calculated from the helical data for a z-axis position of interest. Based on the determined focal lengths, one or more circular scan sinograms, are selected and used in the backprojection of an image point to produce the reconstructed image of the object. Specifically, for each view, and for each image point, the distance of the image point to the detector (in other words, the focal length) is calculated using, for example, a table lookup. Based on the focal length determined for the image point, one or more circular scan sinograms are selected, wherein the selection is performed within a backprojection operation for the image point, for each circular view. One or more of the selected circular scan sinograms are then used in the backprojection of the image point over the circular view. A backprojection for all the image points over all the circular views is then performed to generate a reconstructed image of the object. In a particular embodiment, the circular scan sinogram with the closest focal length determined for image point is used in the back projection of the image point. In addition, interpolation between circular scan sinograms may also be performed based on the plurality of focal lengths corresponding to the circular scan sinograms and the focal length of the image point.

Figure 8:
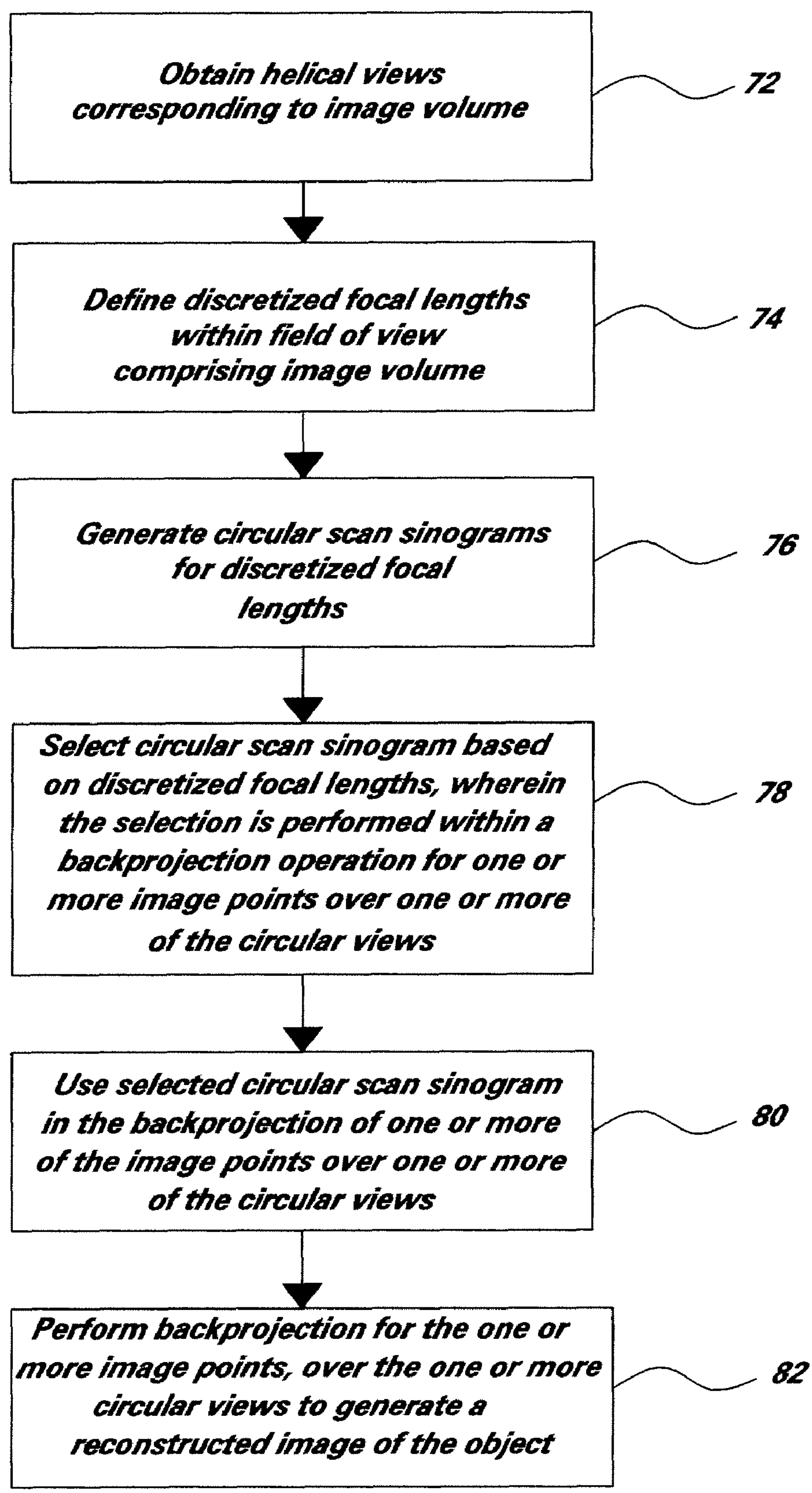
FIG. 8 illustrates one or more process steps for reconstructing an image volume of an object scanned in helical mode, in accordance with an embodiment of the invention.

FIG. 8 illustrates one or more process steps for reconstructing an image volume of an object scanned in helical mode, in accordance with an embodiment of the invention. In step 72, one or more helical views corresponding to an image volume of an object are obtained. In step 74, one or more discrete focal lengths within a field of view comprising the image volume are defined. As mentioned above, the discrete focal lengths represent a plurality of distances of the image point from the detector over a rotation of the X-ray source and the detector about the image volume. In step 76, circular or axial scan sinograms for each of the plurality of discrete focus lengths are generated. As mentioned above, a circular scan sinogram may be computed using standard helical interpolation techniques. In step 78, one or more circular scan sinograms are selected from the plurality of circular scan sinograms, based on the plurality of discrete focal lengths. The selection is performed within a backprojection operation, for one or more image points, over one or more circular views. In step 80, one or more of the selected circular scan sinograms are used in the backprojection of one or more of the image points over one or more of the circular views. In step 82, a backprojection is performed for the one or more image points, over the one or more circular views, to generate a reconstructed image of the object. In one embodiment, a two-dimensional (2D) filtered backprojection reconstruction of the image points is performed to generate the reconstructed image of the object. The resulting 2D filtered backprojection reconstruction possesses high resolution throughout the field of view.

The disclosed embodiments provide a computationally efficient technique for the reconstruction of large image volumes acquired from helical scan acquisitions, with reduced image artifacts and optimized image quality throughout the field of view. The reconstruction technique disclosed in accordance with embodiments of the present invention may be used to reconstruct objects in system topologies having large fields of view and large detector extents. As used herein, a "large field of view" refers to a field of view sufficiently large relative to the acquisition geometry and detector size, resulting in a helical to axial scan approximation with artifacts. As will be appreciated by those skilled in the art, the tolerable artifact level is application dependent, and the divergence of the rays can be neglected by establishing that the divergence of the ray from the point it enters the field of view and exits the field of view is less than the z resolution of the system (or detector size, after scaling to the iso-center).

The disclosed reconstruction technique may also be used in CT applications requiring the reconstruction of large objects at high throughput rates, such as for example in luggage scanning applications and security applications, to enable uniform threat detectability throughout the imaging field of view. The disclosed embodiments may also be used to image objects in CT applications such as industrial CT applications and medical diagnostic CT applications.

The foregoing embodiments show the functionality and operation of a method for reconstructing an image volume of an object scanned in helical mode. In this regard, each block represents a module, segment, or portion of code, which comprises one or more executable instructions for implementing the specified logical function(s). It should also be noted that in some alternative implementations, the functions noted in the blocks may occur out of the order noted in the figures or, for example, may in fact be executed substantially concurrently or in the reverse order, depending upon the functionality involved. Also, one of ordinary skill in the art will recognize that additional blocks may be added.

The above-described method comprises an ordered listing of executable instructions for implementing logical functions. The ordered listing can be embodied in any computer-readable medium for use by or in connection with a computer-based system that can retrieve the instructions and execute them. In the context of this application, the computer-readable medium can be any means that can contain, store, communicate, propagate, transmit or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer readable medium may comprise paper or another suitable medium upon which the instructions are printed. For instance, the instructions can be electronically captured via optical scanning of the paper or other medium, and then compiled, interpreted or otherwise processed in a suitable manner if necessary, and then stored in a computer memory.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for reconstructing an image volume of an object scanned in helical mode, the method comprising:

obtaining one or more helical views corresponding to an image volume of an object;

determining a plurality of discrete focal lengths within an imaging plane of a reconstructed field of view comprising the image volume;

generating a plurality of circular scan sinograms for the plurality of discrete focal lengths, wherein the plurality of circular scan sinograms are generated by interpolating the one or more helical views;

selecting one or more circular scan sinograms, from the plurality of circular scan sinograms, based on the plurality of discrete focal lengths, wherein the selection is performed within a backprojection operation, for one or more image points, over one or more circular views;

using one or more of the selected circular scan sinograms, in the backprojection of one or more of the image points within the imaging plane over one or more of the circular views; and performing a backprojection for the one or more image points, over the one or more circular views to generate a reconstructed image of the object.

2. The method of claim 1, wherein the plurality of discrete focal lengths represent a plurality of distances of the image point within the imaging plane from a detector over a rotation of an X-ray source and the detector about the image volume.

3. The method of claim 2, wherein the plurality of discrete focal lengths are located at a plurality of focal depths along a trajectory followed by the image point within the imaging plane over the rotation of the X-ray source and the detector about the image volume.

4. The method of claim 3, wherein the trajectory followed by the image point is represented by a sinusoidal variation of the discrete focal lengths for the image point from the detector, over the rotation of the X-ray source and the detector about the image volume.

5. The method of claim 1, wherein selecting an appropriate circular scan sonogram further comprises interpolating between one or more of the circular scan sinograms, based on the plurality of discrete focal lengths within the imaging plane.

6. The method of claim 1, wherein the one or more helical views are acquired using a computed tomography (CT) system.

7. The method of claim 6, wherein the CT system is configured to image objects in high-throughput applications.

8. The method of claim 7, wherein the applications comprise at least one of industrial CT applications, security CT applications, and luggage scanning CT applications.

9. The method of claim 1, further comprising performing a two-dimensional (2D) filtered backprojection reconstruction of the one or more image points within the imaging plane to generate the reconstructed image of the object.

10. A computed tomography (CT) system for reconstructing an image volume of an object scanned in helical mode, the computed tomography system comprising:

an X-ray source configured to project a plurality of X-ray beams through the object from a plurality of projection angles;

a detector configured to produce a plurality of electrical signals corresponding to the plurality of X-ray beams; and a processor configured to process the electrical signals to generate one or more helical views corresponding to the imaged object, wherein the processor is configured to:

determine a plurality of discrete focal lengths within an imaging plane of a reconstructed field of view comprising the image volume;

generate a plurality of circular scan sinograms for the plurality of discrete focal lengths, wherein the plurality of circular scan sinograms are generated by interpolating the one or more helical views;

select one or more circular scan sinograms from the plurality of circular scan sinograms, based on the plurality of discrete focal lengths, wherein the selection is performed within a projection operation, for one or more image points within the imaging plane, over one or more circular views; and use one or more of the selected circular scan sinograms, in the backprojection of one or more of the image points over one or more of the circular views; and performing a backprojection for the one or more image points, over the one or more circular views to generate a reconstructed image of the object.

11. The CT system of claim 10, wherein the plurality of discrete focal lengths represent a plurality of distances of the image point within the imaging plane from a detector over a rotation of an X-ray source and the detector about the image volume.

12. The CT system of claim 11, wherein the plurality of discrete focal lengths are located at a plurality of focal depths approximating the trajectory followed by the image point within the imaging plane over the rotation of the X-ray source and the detector about the image volume.

13. The CT system of claim 12, wherein the trajectory followed by the image point within the imaging plane is represented by a sinusoidal variation of the discrete focal lengths from the detector, over the rotation of the X-ray source and the detector about the image volume.

14. The CT system of claim 10, wherein the processor is further configured to select an appropriate circular scan by interpolating between one or more of the circular scan sinograms, based on the based on the plurality of discrete focal lengths.

15. The CT system of claim 10, wherein the CT system is configured to image objects in high throughput applications.

16. The CT system of claim 15, wherein the applications comprise at least one of industrial CT applications, security CT applications and luggage scanning CT applications.

17. The CT system of claim 10, wherein the processor is further configured to perform a two-dimensional (2D) filtered backprojection reconstruction of the one or more image points to generate the reconstructed image of the object.

18. A computer-readable medium storing computer instructions for instructing a computer system for reconstructing an image volume of an object scanned in helical mode, the computer instructions comprising:

obtaining one or more helical views corresponding to an image volume of an object;

determining a plurality of discrete focal lengths within an imaging plane of a reconstructed field of view comprising the image volume;

generating a plurality of circular scan sinograms for the plurality of discrete focal lengths, wherein the plurality of circular scan sinograms are generated by interpolating the one or more helical views;

selecting one or more circular scan sinograms, from the plurality of circular scan sinograms, based on the plurality of discrete focal lengths, wherein the selection is performed within a backprojection operation, for one or more image points within the imaging plane, over one or more circular views;

using one or more of the selected circular scan sinograms, in the backprojection of one or more of the image points over one or more of the circular views; and, performing a backprojection for the one or more image points, over the one or more circular views to generate a reconstructed image of the object.

19. The computer-readable medium of claim 18, wherein the plurality of discrete focal lengths represent a plurality of distances of the image point within the imaging plane from a detector over a rotation of an X-ray source and the detector about the image volume.

20. The computer-readable medium of claim 19, wherein the plurality of discrete focal lengths are located at a plurality of focal depths along a trajectory followed by the image point within the imaging plane over the rotation of the X-ray source and the detector about the image volume.

21. The computer-readable medium of claim 20, wherein the trajectory followed by the focal point is represented by a sinusoidal variation of the discrete focal lengths for the image point within the imaging plane from the detector, over the rotation of the X-ray source and the detector about the image volume.

22. The computer-readable medium of claim 18, wherein selecting an appropriate circular scan sinogram further comprises interpolating between one or more of the circular scan sinograms, based on the plurality of discrete focal lengths.

23. The computer-readable medium of claim 18, further comprising performing a two-dimensional (2D) filtered backprojection reconstruction of the one or more image points to generate the reconstructed image of the object.

* * * * *